United States Patent [19]

Preston et al.

[11] 4,363,332
[45] Dec. 14, 1982

[54] DETECTION OF ROD-LIKE ARTICLES

[75] Inventors: Edward G. Preston; Jan A. Rakowicz, both of London, England

[73] Assignee: Molins Limited, London, England

[21] Appl. No.: 130,956

[22] Filed: Mar. 17, 1980

[30] Foreign Application Priority Data

Mar. 21, 1979 [GB] United Kingdom ................ 7909918

[51] Int. Cl.³ .......................... A24C 5/00; A24C 5/35
[52] U.S. Cl. .................................... 131/282; 131/283; 131/904; 209/535; 209/555; 209/602
[58] Field of Search ................ 131/21 R, 21 B, 21 A, 131/280, 282, 283, 904; 209/535, 555, 602

[56] References Cited

U.S. PATENT DOCUMENTS 3,116,478 12/1963 Powell ................................ 131/904
3,207,308 9/1965 Kemp ................................ 209/535

Primary Examiner—V. Millin
Attorney, Agent, or Firm—John C. Smith, Jr.

[57] ABSTRACT

Cigarettes, as they are grouped in batches to be packed, have their ends detected for firmness or for missing filter tips, by having an array of individually actuated plungers (9) applied to their ends. Each plunger is actuated by air pressure acting on a piston (13) integral with the plunger. If a cigarette (C) is faulty a protuberance (21) on the plunger engages a common impingement plate (20), whose oscillation causes a piezoelectric transducer (22) to emit a fault signal, enabling that cigarette group subsequently to be rejected.

13 Claims, 3 Drawing Figures

DETECTION OF ROD-LIKE ARTICLES

This invention concerns the detection of cigarettes and similar rod-like articles, in particular on machines for packaging groups of cigarettes.

For convenience reference will hereafter be made merely to "cigarettes", which expression is to be understood as including other rod-like articles, such as filter plugs.

In the packaging of cigarettes, it is common to eject groups or bundles of the desired number of cigarettes from the bottom of a vaned hopper, and then to form a package around each group. In order to ensure that each group is complete and to check that the ends of the cigarettes are not unduly soft, it is usual to test each group before it is formed at the bottom of the hopper by using a detecting device which may commonly comprise a group of spring-loaded plungers which are repeatedly urged by a cam mechanism against the ends of each successive group of cigarettes. If any plunger moves an excessive distance into the cigarette group a control switch is made (or alternatively broken), and the resultant fault signal then enables the defective group to be subsequently rejected.

However problems arise on such devices in regard both to vibration caused by high-speed actuation of the cam mechanism, and to unreliability of the switches due to contamination by sparking and by tobacco dust.

According to one aspect of the invention there is provided a device for detecting groups of cigarettes comprising a plurality of plungers engageable with the ends of a group of cigarettes, a body in which said plurality of plungers are mounted for independent movement, the body being fixed in a direction axial of the plungers, pneumatic means operable on the plungers to move each plunger against the end of the respective cigarette of said group, and detection means to detect movement of any plunger beyond a predetermined position relative to said group.

Each plunger may be returned away from the group by a spring; alternatively, or additionally, the pneumatic means may also act on each plunger in a direction away from the group.

The body may be fixedly mounted above an ejection pusher towards the bottom of a cigarette hopper, and the plungers arranged in a rectangular array corresponding to that of the cigarette group being ejected. There may be such a detection device at each side of the hopper so as to engage with both ends of the groups.

According to another aspect of the invention a device for detecting groups of cigarettes comprises a plurality of plungers movably mounted in a body, a fixed detection plate past which the plungers extend, a piezoelectric transducer mounted on said detection plate, an abutment formed on each plunger and engageable with said plate, and actuating means to urge the plungers against a cigarette group, the arrangement being such that if any plunger moves beyond a predetermined position relative to the cigarette group the respective abutment thereof impinges on said detection plate and causes the piezoelectric transducer to produce a fault signal.

The body may, as before, be fixed and the plungers independently movable by pneumatic means, e.g. by a piston integral with each plunger.

An example of a detection device embodying the invention will now be described with reference to the accompanying drawings, in which.

Figure 1:
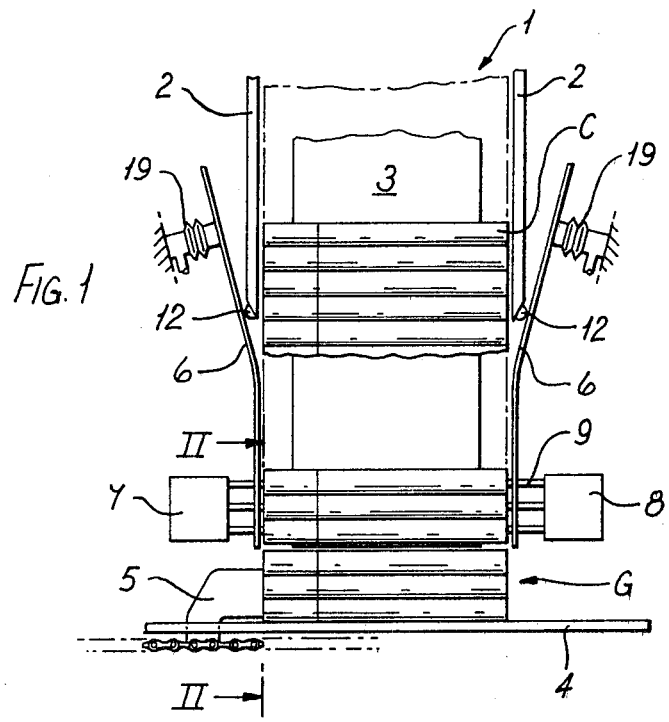
FIG. 1 is a side view of the detection device.
Figure 2:
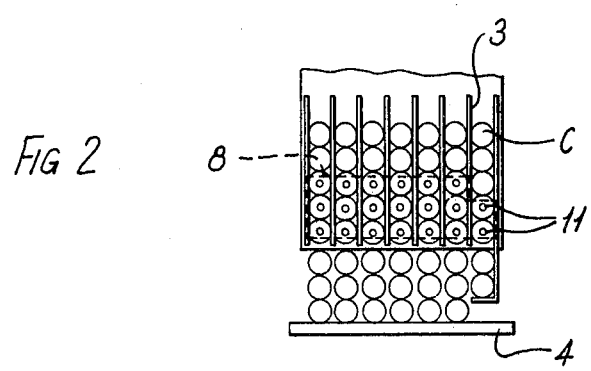
FIG. 2 is an end view of the group of plungers of the device taken on the line II—II of FIG. 1.

Referring first to FIGS. 1 and 2, there is shown the lower part of a cigarette hopper 1 of a packing machine. The hopper is defined by a pair of transparent end walls 2 and eight substantially vertical vanes 3 which form between them seven columns containing filter-tipped cigarettes C. Beneath the hopper is a horizontal bed plate 4, known as the filler bed, along which are arranged to pass a series of pushers 5 (only one shown), each pusher ejecting one group of twenty cigarettes G from under the hopper.

The arrangement described so far is of a known construction, for example as described in greater detail in U.S. Pat. No. 2,621,840. However, in the arrangement shown in FIGS. 1 and 2, the pair of end walls 2 terminate some distance above the pusher 5, and the bottom of each end wall is continued by a gently curved plate 6 pivoted at its upper edge.

Mounted outside the curved plates 6 immediately above the path of the pushers 5 are a pair of feeler devices 7, 8, each comprising an array of twenty plungers 9. The plungers are arranged in seven columns, such that they are aligned with the next group of twenty cigarettes to be ejected by a pusher 5. One of the plungers 9 of the device 8 is shown in the enlarged sectional view of FIG. 3, the plungers of device 7 being similar. The plungers 9 are slidably mounted in a fixed body 10 and their operative ends 11 extend through clearance holes (not shown) in the respective plate 6.

Figure 3:
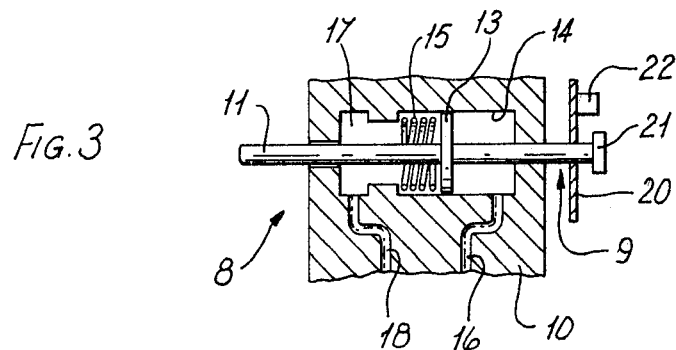
FIG. 3 is a sectional view of one of the plungers, drawn to a larger scale.

The plungers 9 are made of a plastic material, and each is formed with a piston 13 slidable in a bore 14 of the body 10 and biassed to the right, as viewed in FIG. 3, by a compression spring 15. An air passage 16 leads from the right of the bore through a control valve (not shown) to a source of air pressure. To the left of the bore 14 is an annular chamber 17 similarly connected by a passage 18 through the control valve to the source of air pressure. Thus the plunger 9 can be extended to the left by allowing air into passage 16, and returned by the spring 15 with the assistance of air from passage 18.

To the right of the body 10 the plunger 9 passes through an aperture in a plate 20 which is mounted lightly against the back of the body 10. Secured to one edge of the plate 20 is a single piezoelectric transducer 22 (for example, type QZM accelerometer as supplied by Schaevitz E. M., of Slough, England). The extreme right-hand of the plunger is formed with an abutment 21 in the form of an annular shoulder at such a position that when in use the plunger is actuated against a faulty or missing cigarette, the abutment 21 impinges on the plate 20. For this purpose the position of the plate 20 is adjustable relative to the body 10 (by means not shown). The position of the body itself is also adjustable (again by means not shown) to vary the nominal position of the plungers 9 relative to the ends of the group of cigarettes to be detected.

The operation of the cigarette detecting device is as follows:

Commencing with the position shown in FIG. 1, the pusher 5 is about to eject a group G of cigarettes from under the hopper 1. The plungers 9 are fully with-drawn, so that as soon as the group G has been ejected the cigarettes C in each column of the hopper can fall and form the next group. During this time the curved plates 6 are used to vibrate lightly against stops 12 formed on the end walls 2, in order that the ends of the cigarettes are aligned and can fall freely. Such vibration is produced by providing a pulsating air supply to an air bellows 19 mounted on each plate 6 below its pivot point.

The plates 6 then cease to vibrate, coming to rest against the stops 12 in their innermost positions; and with the cigarette group settled in its new position air is supplied to the ports 16 of devices 7 and 8 to extend the plungers 9 against opposite ends of the cigarettes. The location of the ends 11 of the plungers 9, and the spacing between each plate 20 and the abutment 21, is so chosen that if all the cigarettes in the group being tested are satisfactory, the abutment 21 will fail to impinge on the plate 20. However, if on any cigarette the filter tip is missing or the tobacco end is too soft, then the respective plunger 9 will move further until its abutment 21 impinges on the plate 20. The resulting small oscillations caused in the plate 20 are sensed by the piezoelectric transducer 22, which emits a fault signal. A memory device (not shown) receives the fault signal, and subsequently causes that faulty cigarette group to be rejected after it has been pushed out of the hopper 1.

Retraction of the plungers 9 is caused by the springs 15, assisted if necessary by air pressure from the ports 18. The lowermost group is then again ejected by a pusher 5, and the cycle repeated.

It will be appreciated that the device described enables cigarette groups to be detected over a wide range of speeds with great accuracy. This is by virtue of the plungers being independently actuated, and of the force on the plungers being variable during operation of the device, e.g. positional adjustment of the body, and/or variation of the air pressure on the plunger pistons. Furthermore there is only one self-contained sensor for each device, namely a robust piezoelectric transducer, so that there is less likelihood of the device producing spurious fault signals due to malfunctioning.

We claim:

1. In apparatus for forming groups of cigarettes comprising a cigarette hopper, and an ejection pusher at the bottom of said hopper for ejecting successive groups of cigarettes therefrom, the improvement of a device for detecting said groups of cigarettes, said device being mounted at a side of said hopper above said ejection pusher and comprising a plurality of plungers engageable with the ends of a group of cigarettes, a body in which said plurality of plungers are mounted for independent movement, the body being fixed in a direction axial of the plungers, pneumatic means operable on the plungers to move each plunger against the end of the respective cigarette of said group, and piezoelectric transducer means to detect movement of any plunger beyond a predetermined distance into said group.

2. Apparatus according to claim 1 in which a detecting device is mounted at each side of said hopper, so that opposite ends of the cigarettes of said group are detected.

3. Apparatus according to claim 1 in which said plungers are disposed in a substantially rectangular array corresponding to, and positioned immediately above, a cigarette group to be ejected by said ejection pusher.

4. Apparatus according to claim 1 wherein said plungers are slidably mounted in said body and in which said pneumatic means is operable on the plungers to move each plunger independently towards the end of a respective cigarette of said group.

5. Apparatus according to claim 4 wherein said pneumatic means is also operable to return each plunger from the end of said respective cigarette.

6. In apparatus for forming groups of cigarettes, comprising a cigarette hopper and an ejection pusher at the bottom of said hopper for successively ejecting groups of cigarettes therefrom, the improvement of a device for detecting faulty groups of cigarettes, said device being mounted at one side of said hopper above said ejection pusher and comprising:
  (a) a plurality of plungers corresponding in number to the number of cigarettes in a group, each plunger having an end face engageable with the end of a cigarette of a group and having an abutment formed thereon remote from said end face;
  (b) actuating means to independently move said plungers and bring said end faces into engagement with the respective cigarette ends of a group;
  (c) a detection plate disposed between said abutments of said plungers and said cigarette ends of a group; and
  (d) a piezoelectric transducer mounted on said detector plate and adapted to emit a fault signal in response to impingement of an abutment of a plunger with said detection plate;

whereby penetration of a plunger beyond a predetermined distance into a cigarette group causes impingement of the abutment thereof with said detection plate resulting in said transducer emitting a fault signal.

7. In apparatus for forming groups of cigarettes, comprising a cigarette hopper, an ejection pusher at the bottom of said hopper for successively ejecting groups of cigarettes therefrom, the improvement of a device for detecting faulty groups of cigarettes, said device being mounted at one side of said hopper above said ejection pusher and comprising:
  (a) a plurality of plungers, each having an end face engageable with the end of a cigarette of a group;
  (b) actuating means to move said plungers and bring said end faces into engagement with the respective cigarette ends of a group; and
  (c) detection means comprising at least one piezoelectric transducer to detect movement of any plunger beyond a predetermined distance into said group and to emit a fault signal in response to said detected movement;
  (d) whereby any groups of cigarettes having at least one faulty cigarette therein will be detected.

8. Apparatus according to claim 1 further comprising a pivotable member mounted on at least one side of said hopper for engagement with said group, and means for operating said pivotable member prior to movement of said plungers by said actuating means, so that said group is brought into alignment during detection thereof.

9. Apparatus according to claim 7 wherein said plungers are disposed in a substantially rectangular array corresponding to the arrangement of cigarettes in said groups of cigarettes.

10. Apparatus according to claim 7 wherein each of said plungers has an abutment formed thereon remote from said end face and said detection means comprises a detection plate disposed between said abutments of said plungers and said cigarette ends of a group and a piezoelectric transducer mounted on said detector plate and adapted to emit a fault signal in response to impingement of an abutment of a plunger with said detection plate.

11. Apparatus according to claim 7 wherein said actuating means comprises pneumatic means.

12. Apparatus according to claim 11 wherein said pneumatic means is adapted to independently move said plungers.

13. Apparatus according to claim 7 in which a detecting device is mounted at each side of said hopper so that opposite ends of the cigarettes of said group are detected.

* * * * *

UNITED STATES PATENT OFFICE
CERTIFICATE OF CORRECTION

Page 1 of 4

Patent No. 4,363,332  Dated December 14, 1982

Inventor(s) Edward George Preston et al

It is certified that error appears in the above-identified patent and that said Letters Patent are hereby corrected as shown below:

Col. 4, line 53, should read: -- 8. Apparatus according to claim 7 further comprising --.

Col. 6, beginning at line 7, the following claims should be added:

-- 14. Apparatus for detecting faulty or missing cigarettes in successive groups of cigarettes comprising:

a) means for locating successive groups of cigarettes in a predetermined position;

b) a plurality of plungers, each having an end face engageable with the end of a cigarette of a group;

c) actuating means to move said plungers and bring said end faces into engagement with the respective cigarette ends of a group; and d) detection means comprising at least one piezo-electric transducer to detect movement of any plunger beyond a predetermined distance into said group and to emit a fault signal in response to said detected movement;

e) whereby any groups of cigarettes having at least one faulty or missing cigarette therein will be detected.

UNITED STATES PATENT OFFICE
CERTIFICATE OF CORRECTION Page 2 of 4

Patent No. 4,363,332        Dated December 14, 1982

Inventor(s) Edward George Preston et al

It is certified that error appears in the above-identified patent and that said Letters Patent are hereby corrected as shown below:

15. Apparatus according to claim 14 in which a plurality of said plungers is mounted at each of two opposite sides of said means for locating successive groups of cigarettes so that opposite ends of the cigarettes of said group are detected.

16. Apparatus according to claim 14 wherein said plungers are disposed in a substantially rectangular array corresponding to the arrangement of cigarettes in said groups of cigarettes.

17. Apparatus according to claim 14 wherein each of said plungers has an abutment formed therein remote from said end face and said detection means comprises a detection plate disposed between said abutments of said plungers and said cigarette ends of a group and a piezoelectric transducer mounted on said detector plate and adapted to emit a fault signal in response to impingement of an abutment of a plunger with said detection plate.

18. Apparatus according to claim 14 wherein said acutating means comprises pneumatic means.

19. Apparatus according to claim 18 wherein said pneumatic means is adapted to independently move said plungers.

UNITED STATES PATENT OFFICE
CERTIFICATE OF CORRECTION

Patent No. 4,363,332    Dated December 14, 1982

Inventor(s) Edward George Preston et al

It is certified that error appears in the above-identified patent and that said Letters Patent are hereby corrected as shown below:

20. Apparatus for detecting faulty or missing cigarettes in successive groups of cigarettes comprising:

a) means for locating successive groups of cigarettes in a predetermined position;

b) a plurality of plungers, each registering with a different cigarette of a group and each having an end face engageable with the end of a cigarette;

c) actuating means to effect relative movement between said locating means and said plungers to bring said end faces into engagement with the respective ends of satisfactory cigarettes of a group and subsequent relative movement between said locating means and any one of said plungers which does not engage a satisfactory cigarette; and d) piezoelectric transducer means for detecting any one of said plungers not in engagement with a satisfactory cigarette;

UNITED STATES PATENT OFFICE
CERTIFICATE OF CORRECTION

Patent No. 4,363,332     Dated December 14, 1982

Inventor(s) Edward George Preston et al

It is certified that error appears in the above-identified patent and that said Letters Patent are hereby corrected as shown below:

e) whereby any groups of cigarettes having at least one faulty or missing cigarette therein will be detected. --

On the title page "13 Claims" should read
-- 20 Claims --.

Signed and Sealed this

Tenth Day of January 1984

[SEAL]

Attest:

Attesting Officer

GERALD J. MOSSINGHOFF

Commissioner of Patents and Trademarks